United States Patent
Zhao et al.

(10) Patent No.: US 7,345,754 B1
(45) Date of Patent: Mar. 18, 2008

(54) FOURIER FILTERS AND WAFER INSPECTION SYSTEMS

(75) Inventors: Guoheng Zhao, Milpitas, CA (US); Mehdi Vaez-Iravani, Los Gatos, CA (US); Andrew V. Hill, San Jose, CA (US); Avijit K. Ray-Chaudhuri, San Ramon, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 343 days.

(21) Appl. No.: 11/228,584

(22) Filed: Sep. 16, 2005

(51) Int. Cl.
*G01N 21/00* (2006.01)
*G02B 27/46* (2006.01)

(52) U.S. Cl. .............. 356/237.5; 256/237.1; 256/237.2; 359/559

(58) Field of Classification Search .. 356/237.1–237.5; 359/559
See application file for complete search history.

(56) References Cited

U.S. PATENT DOCUMENTS

| | | |
|---|---|---|
| 3,257,563 A | 6/1966 | Laurent |
| 4,330,775 A | 5/1982 | Iwamoto et al. |
| 4,871,257 A | 10/1989 | Suzuki et al. |
| 5,098,191 A | 3/1992 | Noguchi et al. |
| 5,264,912 A | 11/1993 | Vaught et al. |
| 5,276,498 A | 1/1994 | Galbraith et al. |
| 5,440,426 A | 8/1995 | Sandstrom |
| 5,629,768 A | 5/1997 | Hagiwara |
| 5,742,422 A | 4/1998 | Drake |
| 5,798,831 A | 8/1998 | Hagiwara |
| 5,863,712 A * | 1/1999 | Von Bunau et al. ........ 430/396 |
| 5,970,168 A | 10/1999 | Montesanto et al. |
| 6,009,222 A * | 12/1999 | Dong et al. ................ 385/127 |
| 6,020,957 A | 2/2000 | Rosengaus |
| 6,100,971 A | 8/2000 | Imaino et al. |
| 6,538,730 B2 | 3/2003 | Vaez-Iravani et al. |
| 6,608,676 B1 | 8/2003 | Zhao et al. |
| 6,624,880 B2 * | 9/2003 | Sandstrom et al. ........... 355/71 |
| 6,686,602 B2 | 2/2004 | Some |
| 6,724,473 B2 * | 4/2004 | Leong et al. ............ 356/237.2 |
| 6,809,808 B2 | 10/2004 | Feldman et al. |
| 6,853,475 B2 | 2/2005 | Feldman et al. |
| 6,856,931 B2 | 2/2005 | Yoshida |
| 6,870,949 B2 | 3/2005 | Baldwin |

(Continued)

FOREIGN PATENT DOCUMENTS

JP 1-217243 8/1989

(Continued)

*Primary Examiner*—Layla G. Lauchman
*Assistant Examiner*—Jarreas Underwood
(74) *Attorney, Agent, or Firm*—Baker & McKenzie LLP

(57) ABSTRACT

Fourier filters and wafer inspection systems are provided. One embodiment relates to a one-dimensional Fourier filter configured to be included in a bright field inspection system such that the bright field inspection system can be used for broadband dark field inspection of a wafer. The Fourier filter includes an asymmetric illumination aperture configured to be positioned in an illumination path of the inspection system. The Fourier filter also includes an asymmetric imaging aperture complementary to the illumination aperture. The imaging aperture is configured to be positioned in a light collection path of the inspection system such that the imaging aperture blocks light reflected and diffracted from structures on the wafer and allows light scattered from defects on the wafer to pass through the imaging aperture.

24 Claims, 6 Drawing Sheets

U.S. PATENT DOCUMENTS

| | | |
|---|---|---|
| 6,882,417 B2 | 4/2005 | Goldberg et al. |
| 6,908,197 B2 * | 6/2005 | Penn .......................... 353/34 |
| 6,947,199 B2 * | 9/2005 | Roxlo et al. ................ 359/291 |
| 2002/0186944 A1 * | 12/2002 | Riant et al. .................. 385/127 |
| 2003/0117616 A1 | 6/2003 | Nakamura |
| 2004/0042001 A1 | 3/2004 | Vaez-Iravani et al. |
| 2004/0125368 A1 | 7/2004 | Vaez-Iravani |
| 2004/0235208 A1 | 11/2004 | Reinhorn |

FOREIGN PATENT DOCUMENTS

| | | |
|---|---|---|
| JP | 4-204145 | 7/1992 |
| JP | 11-190698 | 7/1999 |

* cited by examiner

FOURIER FILTERS AND WAFER INSPECTION SYSTEMS

BACKGROUND OF THE INVENTION

1. Field of the Invention

This invention generally relates to Fourier filters and wafer inspection systems. Certain embodiments relate to a one-dimensional Fourier filter configured to be included in a bright field inspection system such that the bright field inspection system can be used for broadband dark field inspection of a wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Many different types of inspection tools have been developed for the inspection of semiconductor wafers. Defect inspection is currently being performed using techniques such as bright field (BF) imaging, dark field (DF) imaging, and scattering. The type of inspection tool that is used for inspecting semiconductor wafers may be selected based on, for example, characteristics of the defects of interest and characteristics of the wafers that will be inspected. For example, some inspection tools are designed to inspect unpatterned semiconductor wafers or patterned semiconductor wafers.

Inspection tools for unpatterned wafers are generally not capable of inspecting patterned wafers for a number of reasons. For example, many unpatterned wafer inspection tools are configured such that all of the light collected by a lens or another collector is directed to a single detector that generates a single output signal representative of all of the collected light. Therefore, light scattered from patterns or other features on the specimen will be combined with other scattered light. As such, light scattered from patterns or other features on the wafer can not be separated from other scattered light thereby hindering, if not preventing, defect detection.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the same process tool. Inspection of patterned wafers is, therefore, important to accurately detect defects that may have been formed on the wafer during, or as a result of, processing. Therefore, inspecting patterned wafers or product wafers may provide more accurate monitoring and control of processes and process tools than inspection of monitor wafers.

Many inspection tools have been developed for patterned wafer inspection. Some patterned wafer inspection tools utilize spatial filters to separate light scattered from patterned features from other scattered light such that the other scattered light may be separately detected. Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected.

One type of spatial filter that may be used as described above is a Fourier filter. Fourier filters are relatively useful for filtering light from repetitive patterns such as memory array formed on a wafer. However, Fourier filters can have adverse effects on the transmitted light because the filters are often in the form of periodic blocking bars. These type of filters can diffract light into undesirable directions thereby degrading the imaging quality, which is commonly referred to as ringing or side lobes. Most Fourier filters perform well for inspection systems that use coherent light such as that generated by a laser. However, for inspection systems that use broad band light, it is difficult to use a Fourier filter because the performance of Fourier filters is strongly dependent on wavelength. In addition, the Fourier filter can produce significant distortion at the image plane, which adversely affects the ability of the inspection system to detect defects on the wafer with high accuracy.

Conventional dark field imaging generally uses a circular symmetric illumination aperture with a complementary imaging aperture. While a circular aperture works well for filtering light reflected from wafer, a circular aperture is less than optimum for filtering the light diffracted from repetitive patterns. For example, for many one-dimensional patterns such as metal-1 (M1) repetitive line structures, a conventional dark field aperture does not block all of the diffraction orders completely due to its circular shape. Therefore, such an aperture cannot completely eliminate the pattern and background noise thereby limiting the achievable sensitivity of the system for defect detection on wafers containing one-dimensional or highly asymmetric patterns.

Accordingly, it would be advantageous to develop a Fourier filter that can be used in a bright field inspection system such that the bright field inspection system can be used for broadband dark field inspection of a wafer containing one-dimensional or highly asymmetric patterns and that can substantially eliminate pattern and background noise without producing distortions at the image plane of the system such as ringing.

SUMMARY OF THE INVENTION

The following description of various Fourier filter and system embodiments is not to be construed in any way as limiting the subject matter of the appended claims.

One embodiment relates to a one-dimensional Fourier filter configured to be included in a bright field inspection system such that the bright field inspection system can be used for broadband dark field inspection of a wafer. The Fourier filter includes an asymmetric illumination aperture configured to be positioned in an illumination path of the inspection system. The Fourier filter also includes an asymmetric imaging aperture complementary to the illumination aperture. The asymmetric imaging aperture is configured to be positioned in a light collection path of the inspection system such that the imaging aperture blocks light reflected and diffracted from structures on the wafer and allows light scattered from defects on the wafer to pass through the imaging aperture.

In one embodiment, the imaging aperture is configured to be positioned in the light collection path such that a length of the imaging aperture is substantially perpendicular to a length of the structures. In another embodiment, the light blocked by the imaging aperture includes light reflected and diffracted from the structures that extend lengthwise along a direction substantially perpendicular to a length of the imaging aperture. In a further embodiment, the structures include one-dimensional array patterns. In an additional embodiment, the light blocked by the imaging aperture includes all orders of light diffracted from the structures.

In other embodiments, the light blocked by the imaging aperture does not include light reflected and diffracted from the structures that extend lengthwise along a direction that is not perpendicular to a length of the imaging aperture. In another embodiment, the imaging aperture is configured such that a portion of light diffracted from the structures passes through the imaging aperture.

In some embodiments, the illumination and imaging apertures are configured such that one or more parameters of the illumination and imaging apertures can be altered based on characteristics of the structures. In another embodiment, the illumination and imaging apertures are configured such that an angle of rotation of the illumination and imaging apertures can be altered based on characteristics of the structures.

In one embodiment, a total open area of the illumination aperture is substantially equal to a total open area of the imaging aperture. In another embodiment, the imaging aperture is configured such that the imaging aperture does not produce distortion in images of the wafer generated by the inspection system. Each of the embodiments of the Fourier filter described above may be further configured according to any other embodiment(s) described herein.

Another embodiment relates to a Fourier filter configured to be included in a wafer inspection system. The Fourier filter includes an asymmetric illumination aperture configured to be positioned in an illumination path of the inspection system. The Fourier filter also includes an asymmetric imaging aperture complementary to the illumination aperture. The imaging aperture is configured to be positioned in a light collection path of the inspection system such that the imaging aperture blocks light reflected and diffracted from structures on the wafer and allows light scattered from defects on the wafer to pass through the imaging aperture. Performance of the Fourier filter is substantially independent of wavelength of the wafer inspection system. This embodiment of the Fourier filter may be further configured according to any other embodiment(s) described herein.

An additional embodiment relates to a system configured to inspect a wafer. The system includes a broadband light source configured to generate incoherent light. The system also includes an asymmetric illumination aperture arranged in a path of the light such that light that passes through the illumination aperture illuminates the wafer. In addition, the system includes an asymmetric imaging aperture complementary to the illumination aperture. The imaging aperture is configured to block light reflected and diffracted from structures on the wafer and to allow light scattered from defects on the wafer to pass through the imaging aperture. The system further includes a detector configured to generate output signals responsive to the light that passes through the imaging aperture. The output signals can be used to detect the defects on the wafer.

In one embodiment, the imaging aperture is arranged at a Fourier plane of the system. In another embodiment, a length of the imaging aperture is substantially perpendicular to a length of the structures.

In a further embodiment, the light blocked by the imaging aperture includes light reflected and diffracted from the structures that extend lengthwise along a direction substantially perpendicular to a length of the imaging aperture. In another embodiment, the structures include one-dimensional array patterns. In an additional embodiment, the light blocked by the imaging aperture includes all orders of light diffracted from the structures. In other embodiments, the light blocked by the imaging aperture does not include light reflected and diffracted from the structures that extend lengthwise along a direction that is not perpendicular to a length of the imaging aperture.

In one embodiment, the system is configured to alter one or more parameters of the illumination and imaging apertures based on characteristics of the structures. In another embodiment, the system is configured to alter an angle of rotation of the illumination and imaging apertures based on characteristics of the structures. In a further embodiment, the system is configured to alter one or more parameters of the illumination and imaging apertures such that a portion of light diffracted from the structures passes through the imaging aperture.

In some embodiments, a total open area of the illumination aperture is substantially equal to a total open area of the imaging aperture. In yet another embodiment, the imaging aperture is configured such that the imaging aperture does not produce distortion in the output signals generated by the detector. Each of the embodiments of the system described above may be further configured according to any other embodiment(s) described herein.

BRIEF DESCRIPTION OF THE DRAWINGS

Other objects and advantages of the invention will become apparent upon reading the following detailed description and upon reference to the accompanying drawings in which.

Figure 1:
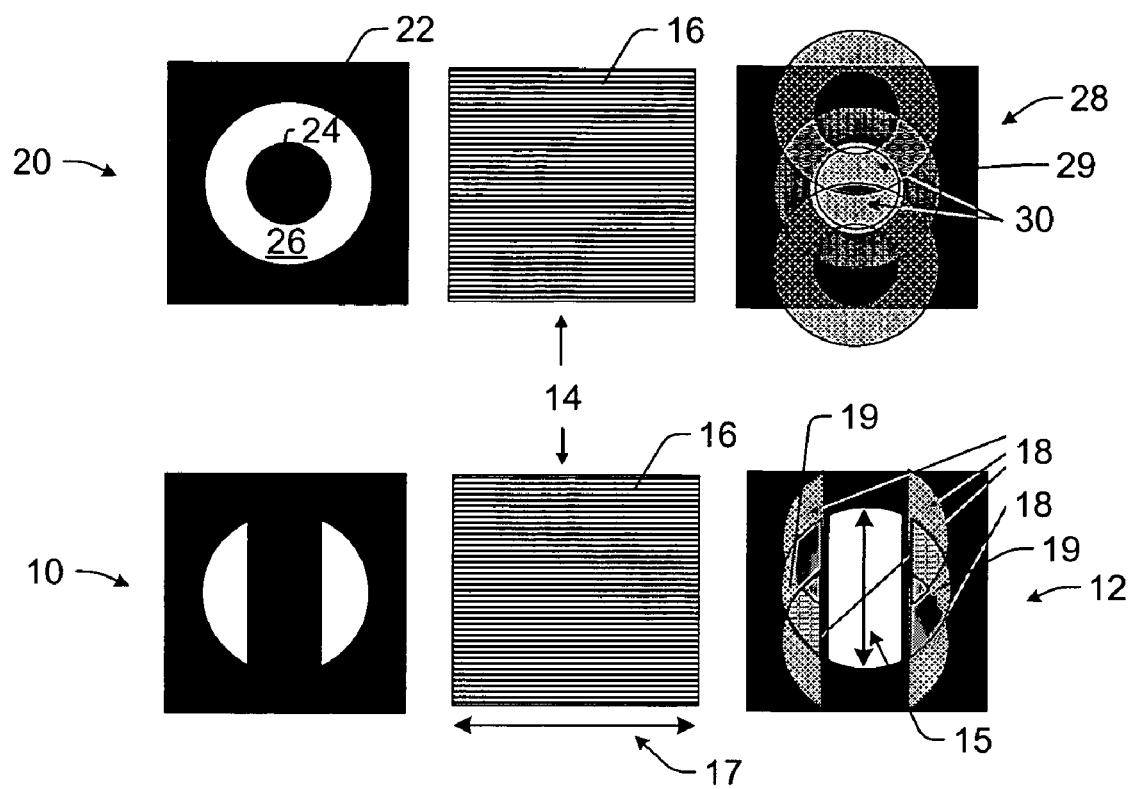
FIG. 1 is a schematic diagram illustrating top views of one example of a previously used dark field aperture and one embodiment of a Fourier filter.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the one-dimensional Fourier filter embodiments described herein may be included in a bright field inspection system such that the bright field inspection system can be used for broadband dark field inspection of another specimen such as a reticle, which may also be commonly referred to as a mask or a photomask. Many different types of reticles are known in the art, and the terms "reticle," "mask," and "photomask" as used herein are intended to encompass all types of reticles known in the art.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a one-dimensional Fourier filter configured to be included in a bright field inspection system. The bright field inspection system may be configured as described further herein. In addition, the Fourier filter is configured such that the bright field inspection system can be used for broadband dark field inspection of a wafer. Such inspection may be generally referred to as one-dimensional dark field imaging mode. Furthermore, although the one-dimensional Fourier filter embodiments are described herein as configured to be included in an inspection system for broadband dark field inspection of a wafer, it is to be understood that the one-dimensional Fourier filter embodiments are also suitably configured to be included in a bright field inspection system such that the inspection system can be used for narrowband dark field inspection of a wafer. Such embodiments will have all of the advantages of the one-dimensional Fourier filter embodiments described herein including, for example, substantial elimination of ringing or other distortion of the images of the wafer generated by the narrowband inspection system.

As shown in FIG. 1, the Fourier filter includes asymmetric illumination aperture 10 configured to be positioned in an illumination path of the inspection system. The Fourier filter also includes asymmetric imaging aperture 12 that is complementary to illumination aperture 10. The illumination and imaging apertures are asymmetric in that they are not circular apertures or apertures having openings of some other symmetric shape. The openings in the illumination and imaging apertures shown in FIG. 1 are shown in white, and the substantially opaque portions of the apertures are shown in black. The apertures are located at the conjugate image planes of each other in the optical paths of illumination and imaging such that light can pass through the openings but not the substantially opaque portions of the apertures. Imaging aperture 12 is configured to be positioned in a light collection path of the inspection system such that the imaging aperture blocks light reflected and diffracted from structures 16 on wafer 14 and allows light scattered from defects (not shown) on the wafer to pass through the imaging aperture.

In one embodiment, the imaging aperture is configured to be positioned in the light collection path such that length 15 of the imaging aperture is substantially perpendicular to length 17 of structures 16 formed on wafer 14. As shown in FIG. 1, the illumination aperture may also have a similar position with respect to the length of structures 16 formed on wafer 14. As such, the illumination and imaging apertures may be positioned with respect to the orientation of the patterned structures in the wafer plane. In such a position, light 19 blocked by imaging aperture 12 includes light reflected by structures 16 on wafer 14, and light 18 blocked by imaging aperture 12 includes light diffracted from structures 16 on wafer 14. In this manner, the imaging aperture blocks light reflected and diffracted from structures on the wafer that extend lengthwise along a direction that is substantially perpendicular to a length of the imaging aperture. In some embodiments, the light that is blocked by the imaging aperture of the Fourier filter embodiments described herein does not include light diffracted from structures on the wafer that extend lengthwise along a direction that is not perpendicular to a length of the imaging aperture.

As further shown in FIG. 1, structures 16 formed on wafer 14 generally include a one-dimensional array of patterns. In other words, the structures on wafer 14 have a substantial length in only one dimension and therefore a substantial pitch in only one dimension. In this manner, the light blocked by the imaging aperture may include light reflected and diffracted from one-dimensional array patterns on the wafer. In another embodiment, the light blocked by the imaging aperture includes all orders of light diffracted from the structures on the wafer. For instance, as shown in FIG. 1, the imaging aperture is configured such that none of light 18 diffracted from structures 16 on wafer 14 is directed through the imaging aperture. In other words, the imaging aperture is configured such that all orders of diffracted light from structures 16 on wafer 14 impinge on the substantially opaque regions of the imaging aperture.

In contrast, illumination aperture 20 is an illumination aperture that is commonly included in a bright field inspection system such that the bright field inspection system can be used for broadband dark field inspection of a wafer. As shown in FIG. 1, illumination aperture 20 is a circular, symmetric aperture. In particular, illumination aperture 20 includes two substantially opaque regions 22 and 24 both of which have a circular, symmetric shape surrounding transparent region 26. In addition, imaging aperture 28 that is commonly used with illumination aperture 20 includes a circular symmetric opening that is complementary to the opening in illumination aperture 20.

As shown in FIG. 1, when illumination aperture 20 and imaging aperture 28 are included in an inspection system during inspection of wafer 14 that includes structures 16 that are relatively one-dimensional (i.e., the structures have a lateral extent in one dimension that is substantially larger than the lateral extent of the structures in the opposite direction), a substantial amount of diffracted light 30 from the structures on the wafer will pass through the imaging aperture. In other words, previously used dark field apertures such as apertures 20 and 28 will block 0th order light 29 (reflected light) from a one-dimensional array of patterns, but the higher diffraction orders (only the 1st orders of diffracted light 30 are shown in this example) will pass through the imaging aperture thereby creating background pattern noise in output signals generated by an inspection system in which the dark field aperture is included.

In this manner, for array inspections, conventional dark field apertures are not optimized when the array pitch is not substantially small (as is the case for one-dimensional array patterns in which the structures have a substantial lateral dimension in one dimension and therefore a substantial pitch in that dimension). The conventional dark field modes are even less optimized when such relatively large pitch arrays are inspected with shorter wavelengths (e.g., wavelengths shorter than 400 nm) such as those used in advanced imaging inspection systems such as the 23XX series of tools that are commercially available from KLA-Tencor, San Jose, Calif. Such pattern and wavelength combinations result in the diffraction orders passing though the imaging aperture thereby resulting in higher background noise in the detector images.

Figure 2:
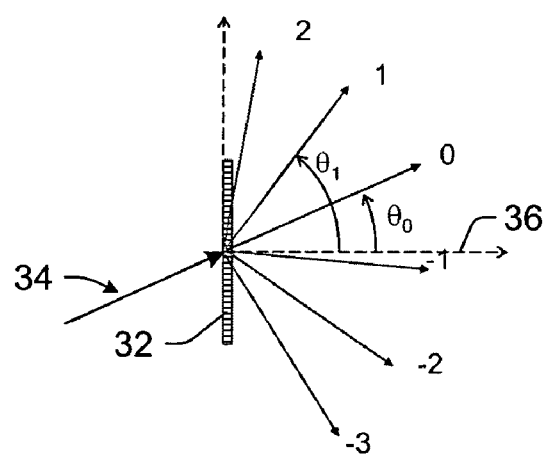
FIG. 2 is a schematic diagram illustrating different orders of light diffracted from a grating calculated using diffraction equations.

Such a relationship between array pitch, wavelength, and propagation direction of diffracted light is illustrated in FIG. 2. In particular, FIG. 2 illustrates the propagation directions of different orders of light diffracted from grating 32. The propagation directions of the diffracted light can be calculated from the following diffraction equation:

$$\sin\theta_m - \sin\theta_o = m\frac{\lambda}{d}$$

where $\lambda$ is wavelength, d is grating period (array pitch), m is the order number, $\theta_m$ (m=0, ±1, ±2, ±3, . . . ) is the propagation angle of the $m^{th}$ diffraction order, and $\theta_0$ is the incident angle, or the range of angles within the illumination aperture.

As shown in FIG. 2, incident beam of light 34 illuminates grating 32 that includes an array of one-dimensional structures. As further shown in FIG. 2, the different diffraction orders (0, 1, 2, etc.) propagate along directions at some angle ($\theta_0, \theta_1, \theta_2, \ldots \theta_m$, etc.), respectively, from reference axis 36. The 0th order light is the light reflected or transmitted by the grating, and the direction of the 0th order light is independent of wavelength and array pitch. However, the propagation directions of the diffracted orders of light are determined by wavelength of illumination and array pitch. In general, as the wavelength decreases, the angle of diffraction at which the diffracted orders of light propagate from the grating decreases, which results in the diffracted orders of light being passed through the previously used dark field apertures.

Figure 3:
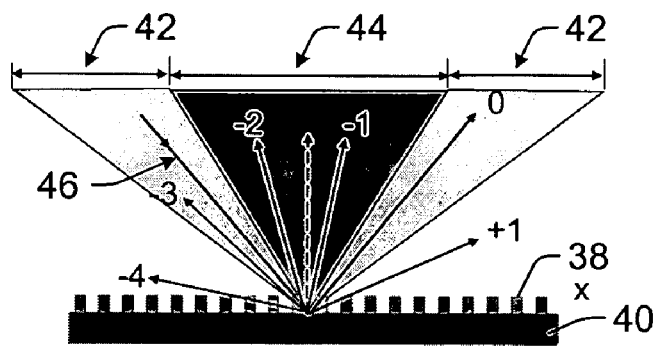
FIG. 3 is a schematic diagram illustrating a side view of different orders of light diffracted by an array pattern formed on a wafer calculated using diffraction equations.

FIG. 3 also illustrates the diffraction orders from an array of one-dimensional structures 38 on wafer 40 with respect to the previously used dark field aperture illustrated in FIG. 1. For instance, the previously used dark field aperture has illumination NA 42 shown in FIG. 3, which is defined by illumination aperture 20 shown in FIG. 1. In addition, the previously used dark field aperture has imaging NA 44 shown in FIG. 3, which is defined by imaging aperture 28 shown in FIG. 1. As shown in FIG. 3, incident wave of light 46 is directed to structures 38 on wafer 40 through illumination NA 42 of the illumination aperture. As a result of illumination, diffraction orders of light indicated in FIG. 3 by their corresponding order number (e.g., −4, −3, −2, −1, 0, and +1) propagate from wafer 40. The location of the higher orders of diffraction are determined by array pitch and wavelength as described above in addition to the angle of illumination as defined by the illumination aperture.

An array pattern is "resolved" when at least two diffraction orders (including the 0th order) are collected by the objective (not shown) of an inspection system. In dark field mode, the $0^{th}$ order is always blocked by the imaging aperture. However, as shown in FIG. 3, if two orders of diffracted light (e.g., −2 and −1) propagate along directions located within imaging NA 44 defined by the imaging aperture, the array pattern from wafer is "resolved" which results in excessive background pattern noise.

Figure 4:
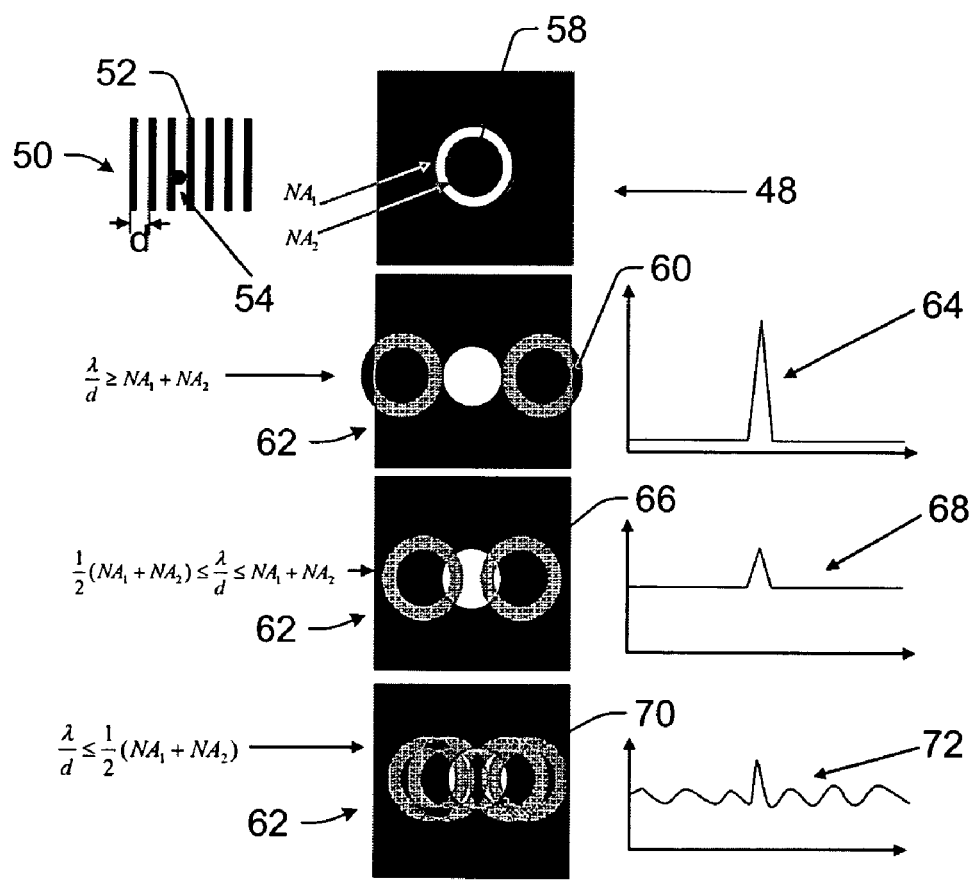
FIG. 4 is a schematic diagram illustrating a top view of one example of a previously used dark field aperture and changes in the background and pattern noise of light passed through the aperture for different ratios of illumination wavelength to pitch of patterned structures on a wafer.

FIG. 4 further illustrates the effect that the ratio between wavelength and array pitch has on the background and pattern noise in output signals of an inspection system that includes the previously used dark field aperture shown in FIG. 1. In particular, illumination aperture 48 may be positioned in an illumination path of an inspection system such that light passing through the illumination aperture illuminates wafer 50. Wafer 50 includes an array of patterned structures 52 that are one-dimensional and have pitch d. In addition, wafer 50 includes defect 54 located within the array of patterned structures. Illumination aperture 48 has a first numerical aperture, $NA_1$, which corresponds to the outer boundary of opening 58 defined by the outer substantially opaque region of the illumination aperture, and a second numerical aperture, $NA_2$, which corresponds to the inner boundary of opening 58 defined by the inner substantially opaque region of the illumination aperture.

As further shown in FIG. 4, when the ratio of wavelength to pitch is greater than or equal to the sum of the two numerical apertures of the illumination aperture $\left(\frac{\lambda}{d}\right)$ $$\left(i.e., \frac{\lambda}{d} \geq NA_1 + NA_2\right),$$

light 60 diffracted from pattern structures 52 is spaced laterally from imaging aperture 62. In this manner, output signal 64 responsive to the light that passes through the imaging aperture has low background and pattern noise since all of the diffraction orders are outside of the imaging aperture. Therefore, for such a relationship between the wavelength, pitch, and two numerical apertures of the illumination aperture, the signal-to-noise ratio of the output signals will be relatively high resulting in high defect detection sensitivity.

In contrast, when the ratio of wavelength to pitch is greater than or equal to one half of the sum of the two numerical apertures of the illumination aperture and less than or equal to the sum of the two numerical apertures of the illumination aperture $$\left(i.e., 1/2(NA_1 + NA_2) \leq \frac{\lambda}{d} \leq (NA_1 + NA_2)\right),$$

light 66 diffracted from pattern structures 52 is partially located within imaging aperture 62. In this manner, output signal 68 responsive to the light that passes through the imaging aperture has high background noise although no pattern is imaged since the portions of the +/−1 orders that pass through the imaging aperture are incoherent since they are from different parts of the illumination ring of the incoherent illumination. The increased background noise eliminates part of the useful dynamic range of the imaging sensor thereby relatively reducing the signal. There is also increased shot noise due to increased background noise. Therefore, for such a relationship between the wavelength, pitch, and two numerical apertures of the illumination aperture, the signal-to-noise ratio of the output signals will be relatively low thereby resulting in relatively low defect detection sensitivity.

As further shown in FIG. 4, when the ratio of wavelength to pitch is less than or equal to one half of the sum of the two numerical apertures of the illumination aperture $$\left(i.e., \frac{\lambda}{d} \leq 1/2(NA_1 + NA_2)\right),$$

light 70 diffracted from pattern structures 52 is partially located within imaging aperture 62. As such, output signal 72 responsive to the light that passes through the imaging aperture has high background noise, and pattern structures are imaged since the +/−2 orders are collected. The portion of the +1 and +2 (and the portion of the −1 and −2 orders) originating from the same point of the illumination aperture are coherent and form a pattern image. In addition to the drawbacks of high background discussed in the previous paragraph, the pattern present in the image contributes to extra noise that can not be completely removed by cell to cell subtractions. Therefore, for such a relationship between the wavelength, pitch, and two numerical apertures of the illumination aperture, the signal-to-noise ratio of the output signals will be relatively low with substantial pattern noise thereby resulting in relatively poor defect detection sensitivity.

As described above, therefore, light diffracted and reflected from pattern structures that passes through the imaging aperture will adversely affect the defect detection capability of the inspection system since such light may create noise in the output signals generated by the inspection system. In addition, since the light diffracted and reflected from such structures may be relatively intense, this light may obscure light scattered from defects on the wafer by using too much of the dynamic range of the imaging sensor.

In contrast, since the Fourier filter embodiments described herein are configured to block all diffraction orders of light from one-dimensional structures, the Fourier filter embodiments described herein substantially eliminate pattern and background noise from output signals of an inspection system. As such, the Fourier filter embodiments described herein may be used to increase the signal-to-noise ratio of the light detected by the inspection system that is scattered from defects on the wafer. In this manner, an inspection system that includes a Fourier filter as described herein will have relatively good sensitivity for defect detection on patterned wafers that include one-dimensional structures.

Figure 5:
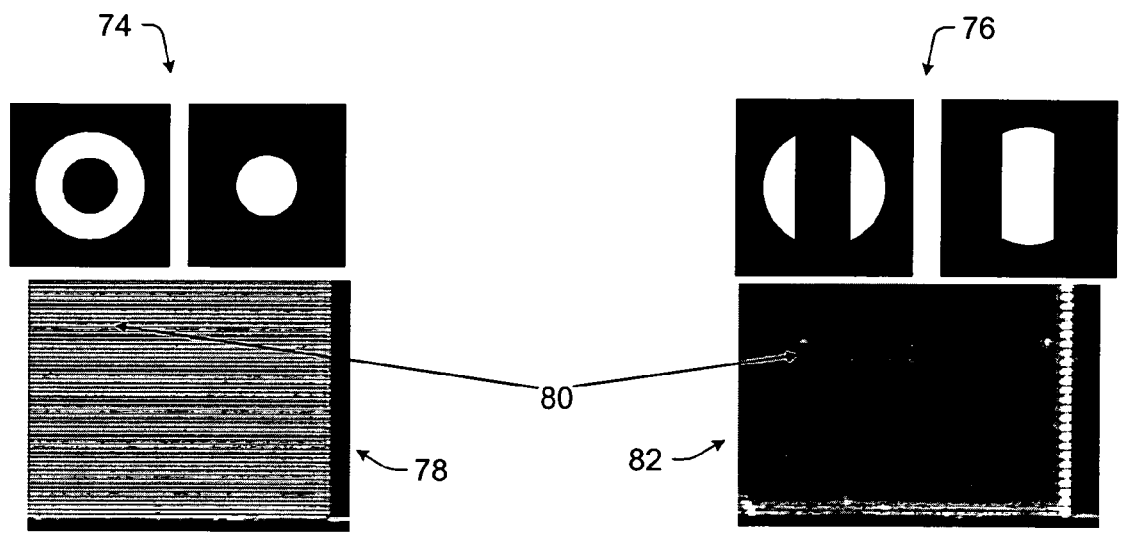
FIG. 5 is a schematic diagram illustrating top views of one example of a previously used dark field aperture and one embodiment of a Fourier filter and images generated using the dark field aperture and the Fourier filter embodiment.

Such differences between the output signals detected using conventional dark field mode and the embodiments of the Fourier filters described herein are further illustrated in FIG. 5. In particular, FIG. 5 illustrates conventional dark field aperture 74 and one embodiment of one-dimensional Fourier filter 76 that were included in a bright field inspection system such that the inspection system could be used for broadband dark field inspection of a wafer. The images shown in FIG. 5 and described further below were generated using visible wavelength illumination.

As further shown in FIG. 5, image 78 of a wafer on which an array of one-dimensional pattern structures is formed was generated by the inspection system using conventional dark field aperture 74. As shown in image 78, the one-dimensional pattern structures are imaged by the system using dark field aperture 74. Therefore, the one-dimensional pattern structures reduce the signal-to-noise ratio of defect 80 that is located within the array of one-dimensional pattern structures. In contrast, image 82 of the same wafer was generated by the inspection system using Fourier filter 76. As shown in image 82, the one-dimensional pattern structures are not imaged by the system when using Fourier filter 76. In this manner, the one-dimensional pattern structures do not reduce the signal-to-noise ratio of defect 80 that is located within the array of one-dimensional pattern structures. In contrast with image 78, defect 80 appears relatively bright in image 82 with respect to the background.

In one embodiment, the illumination and imaging apertures are configured such that one or more parameters of the illumination and imaging apertures can be altered based on characteristics of structures on the wafer. For example, both the illumination and imaging apertures may be made programmable (adjustable). In one such embodiment, the illumination aperture may include two relatively thin strips of substantially opaque bars that are closely overlapped one on top of the other.

Figure 6:
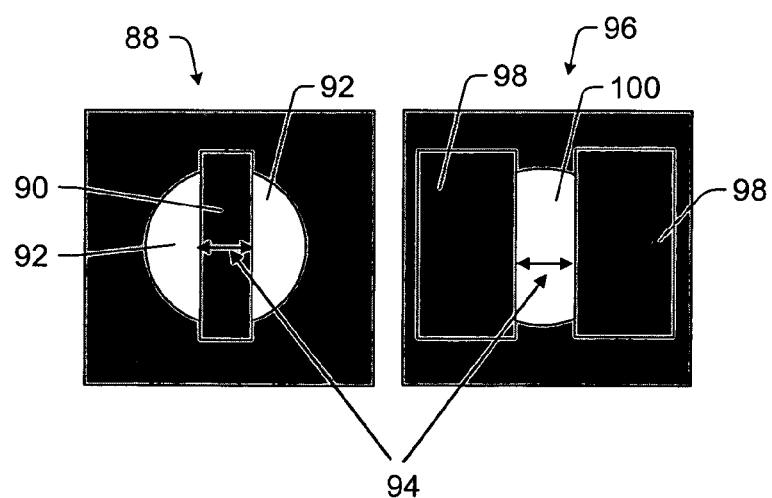
FIG. 6 is a schematic diagram illustrating a top view of one embodiment of a Fourier filter having one or more alterable parameters.

One such embodiment is illustrated in FIG. 6. In particular, as shown in FIG. 6, illumination aperture 88 includes two substantially opaque bars 90, which in this figure are shown completely overlapped with each other so that only the top opaque bar is shown in FIG. 6. To alter the dimensions of openings 92 of illumination aperture 88, the two substantially opaque bars may be moved in opposite directions 94. In this manner, the blockage of the illumination aperture can be adjusted by changing the relative position of the two substantially opaque bars.

In such embodiments, the imaging aperture may be a variable width slit aperture that is complementary to the illumination aperture. For instance, as shown in FIG. 6, in one embodiment, imaging aperture 96 includes two substantially opaque bars 98, which are spaced from each other. The spacing between the two substantially opaque bars defines opening 100 of imaging aperture 96. Therefore, the two substantially opaque bars may be moved in opposite directions 94 to alter the dimensions of opening 100.

The substantially opaque bars of the illumination and imaging apertures may be coupled to any suitable mechanical or other assembly that can be configured to effectuate movement of the substantially opaque bars of the apertures. In addition, the substantially opaque bars of the illumination and imaging apertures may be coupled to different such assemblies. The assemblies may be controlled by a processor of an inspection system, both of which may be configured as described herein.

In some embodiments, a total open area of the illumination aperture is substantially equal to a total open area of the imaging aperture. For example, the positions of the substantially opaque bars may be altered as described above such that the illumination and imaging apertures are completely complementary to one another. By setting the total area of opening in the illumination aperture to be equal to that of the imaging aperture, the size of the illumination aperture and the imaging aperture may be optimized for maximum light efficiency.

Some patterned structures formed on wafers produce a two-dimensional array of diffraction orders at the back focal plane of an inspection system. Such diffraction patterns may be produced by patterned structures that have pitches in two opposing directions that are large enough to generate propagating diffraction orders. In this manner, such patterned structures are two-dimensional array patterns for the applications described herein. In addition, differences between the pitches of the patterned structures in opposite directions may cause the two-dimensional array of diffraction orders at the back focal plane (or the relayed conjugate plane) of the objective of the inspection system to be offset in one direction with respect to the x and y axes on the wafer. As such, the locations of the diffraction orders within a two-dimensional diffraction pattern at the back focal plane of the objective of the inspection system may vary depending on the characteristics of the patterns formed on the wafer.

Figure 7:
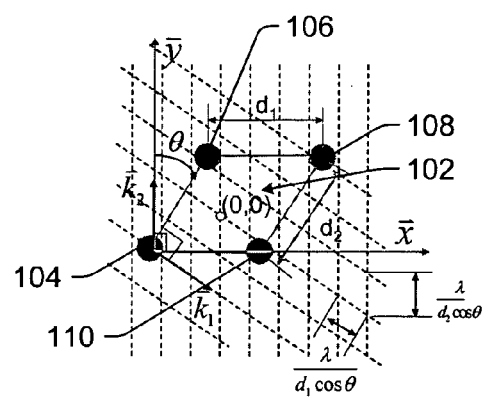
FIG. 7 is a schematic diagram illustrating a map of diffraction orders from a two-dimensional array calculated using diffraction equations.

FIG. 7 illustrates one example of a map of a two-dimensional array of diffraction orders for an array unit cell that is not aligned with the x and y axes on the wafer. In particular, FIG. 7 illustrates the diffraction orders in the NA space (e.g., at the back focal plane of the objective) from array unit cell 102 overlapped with the x and y axes on the wafer. Array unit cell 102 is defined by the lines drawn between corners 104, 106, 108, and 110. As shown in FIG. 7, $\vec{k}_1$ and $\vec{k}_2$ are the unit vectors defining the location of the diffraction orders at the back focal plane of the objective. $\vec{k}_1$ is perpendicular to one side of unit cell 102 connected by corners 104 and 106, and $\vec{k}_2$ is perpendicular to the other side of unit cell 102 connected by corners 104 and 110. The diffraction orders in NA space are located at the cross points of the dotted lines, which are parallel to $\vec{k}_1$ and $\vec{k}_2$ respectively. In addition, array unit cell 102 is tilted at an angle θ with respect to the y axis, which produces a corresponding tilt in the two-dimensional array of diffraction orders at the back focal plane. The array unit cell has dimensions $d_1$ and $d_2$ as shown in FIG. 7. The spacing between the diffraction orders is given by:

$$\frac{\lambda}{d_1 \cos\theta} \text{ and } \frac{\lambda}{d_2 \cos\theta} \text{ along } \vec{k}_1 \text{ and } \vec{k}_2$$

respectively, as shown in FIG. 7.

Accordingly, for array unit cell 102 on a wafer (not shown in FIG. 7), the two-dimensional array of diffraction orders shown in FIG. 7 will be tilted with respect to the configurations of the Fourier filter embodiments described above. However, in some embodiments, the illumination and imaging apertures are configured such that an angle of rotation of the illumination and imaging apertures can be altered based on characteristics of structures on the wafer. In this manner, to further optimize the apertures, a rotation can be applied to both the illumination and imaging apertures, such that the apertures can be aligned with non-rectangular unit cells.

Figure 8:
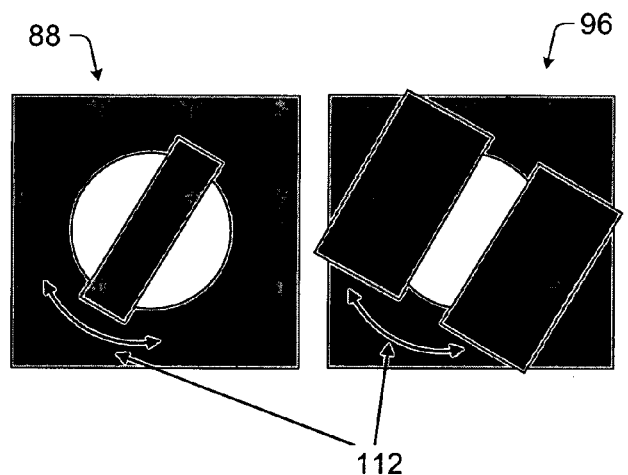
FIG. 8 is a schematic diagram illustrating a top view of another embodiment of a Fourier filter having one or more alterable parameters.

In particular, as shown in FIG. 8, illumination aperture 88, which may be configured as described above, may also be configured such that it can be rotated along directions 112. In addition, as shown in FIG. 8, imaging aperture 96, which may be configured as described above, may also be configured such that it can be rotated along directions 112. In this manner, the orientations of the illumination and imaging apertures are adjustable. The angle of rotation of the illumination and imaging apertures may be controlled as described further above.

Figure 9:
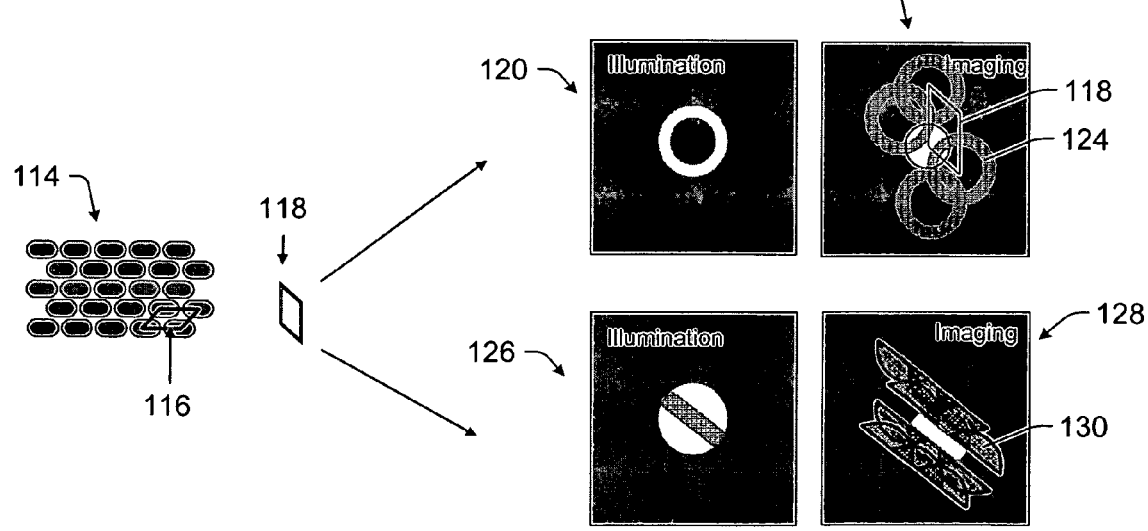
FIG. 9 is a schematic diagram illustrating top views of one example of a wafer pattern and diffraction of light from the wafer pattern with respect to one example of a previously used dark field aperture and one embodiment of a Fourier filter.

FIG. 9 illustrates one example of a two-dimensional pattern array that may be formed on a wafer and that may benefit from an angular orientation-adjustable Fourier filter as described in the above embodiments. For example, as shown in FIG. 9, two-dimensional array 114 of patterned structures may be formed on a wafer (not shown in FIG. 9). As further shown in FIG. 9, the patterned structures of two-dimensional array 114 have a dimension and therefore pitch in one direction that is much larger than the dimension and pitch of the patterned structures in the opposite direction. In this manner, unit cell 116 of the two-dimensional array is tilted in one direction. Accordingly, when illuminated, the unit cell produces diffraction pattern 118 at the back focal plane of an objective of the inspection system. As further shown in FIG. 9, the unit cell of diffraction pattern is tilted in one direction at the back focal plane and has a spacing between diffraction orders in one direction that is much larger than the spacing in the opposite direction.

The differences between the ability of conventional dark field apertures and Fourier filter embodiments described herein to block the diffraction pattern of this unit cell are further shown in FIG. 9. In particular, a conventional dark field aperture that includes illumination aperture 120 and imaging aperture 122, which may be configured as described above, may be included in an inspection system for inspection of the wafer that includes unit cell 116. As shown in FIG. 9, the position of diffraction pattern 118 with respect to imaging aperture 122 causes some of diffracted light 124 to pass through imaging aperture 122. The diffracted light will contribute to background and pattern noise as described above.

In contrast, an embodiment of a Fourier filter that includes illumination aperture 126 and imaging aperture 128, which may be configured as described above, may be included in an inspection system for inspection of the wafer that includes unit cell 116. As shown in FIG. 9, the orientation of illumination aperture 126 and imaging aperture 128 may be rotated with respect to the patterned structures formed on the wafer. In this manner, the imaging aperture may be configured in some embodiments such that the length of the imaging aperture is not substantially perpendicular to a length of structures formed on the wafer. Instead, the imaging aperture may be positioned in the light collection path such that the length of the imaging aperture is arranged based on the orientation of the diffraction pattern at the back focal plane of the inspection system. In this manner, such rotation of the apertures may be selected to correspond to the tilting of the diffraction pattern of the unit cell. As such, as shown in FIG. 9, the position of the diffraction pattern with respect to imaging aperture 128 results in all of diffracted light 130 being blocked by imaging aperture 128.

In this manner, the diffracted light from unit cell 116 cannot increase the background and pattern noise in the light passed through imaging aperture 128 thereby resulting in a higher signal-to-noise ratio for defect detection. As such, for some two-dimensional array patterns, when the pitch in one direction is small enough (sufficiently small values of pitch can be determined according to the equations described above), the Fourier filter embodiments described herein can effectively block all diffraction orders. On the other hand, conventional dark field apertures allow some diffraction orders to pass through their imaging apertures due to diffraction in the large pitch direction.

In some embodiments, the imaging aperture is configured such that a portion of light diffracted from structures on the wafer passes through the imaging aperture. For example, in some applications in which the images of some structures (e.g., structures that define breaks in the active areas or array structures of memory cells) are useful features for defect classification, the illumination aperture and imaging aperture can be modified such that the scattered light (the dark field signal) of selected line features is allowed to leak (or partially pass) through the imaging aperture. The shape and dimensions of the illumination and imaging apertures may be selected to control the magnitude of the leaked light, and therefore the relative intensity of the line features in the image. In general, the optimum conditions for such applications are that the intensity of the selected line features in the final images is strong enough for extracting the useful classification information, but not too strong to degrade the overall signal-to-noise ratio of defects of interest.

Figure 10:
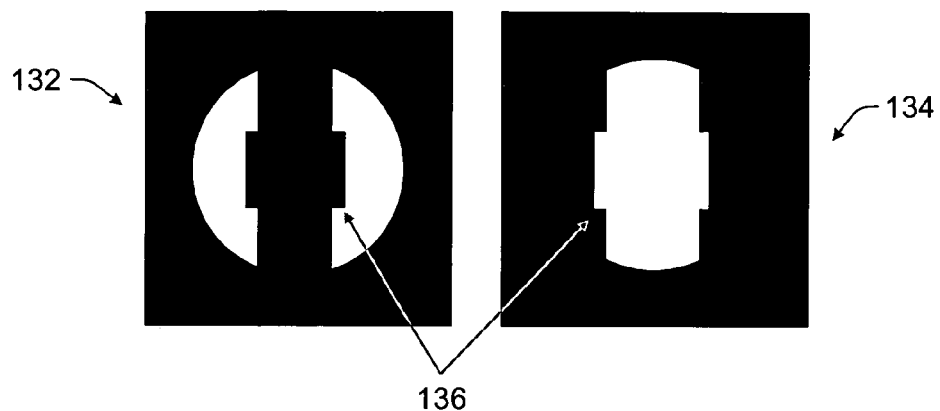
FIG. 10 is a schematic diagram illustrating a top view of a different embodiment of a Fourier filter.

FIG. 10 illustrates one embodiment of a Fourier filter that is configured such that a portion of light diffracted from structures on the wafer passes through the imaging aperture. In particular, this embodiment of a Fourier filter includes illumination aperture 132 and imaging aperture 134. As shown in FIG. 10, both the illumination aperture and the imaging aperture include relatively small deviations 136 from the embodiments of the Fourier filters described herein. Other than deviations 136, the illumination and imaging apertures shown in FIG. 10 may be further configured as described herein.

The deviations in the illumination and imaging apertures are configured to allow leakage of dark field light through the imaging aperture from wanted line features. Such apertures may be adjustable as described further above. For instance, the non-deviated apertures described above may include additional substantially opaque bars that may be moved as described above. In addition, the additional substantially opaque bars may have dimensions that are different than the other substantially opaque bars described above. In this manner, when leakage of light from some patterned structures is desired, the Fourier filters described above may be modified by moving the additional substantially opaque bars beyond the outer lateral edges of the other substantially opaque bars to cause the deviations shown in FIG. 10. In addition, the degree to which the additional substantially opaque bars extend beyond the other substantially opaque bars may be altered depending on how much of the light diffracted from wanted pattern structures is desired.

Alternatively, an inspection system configured as described herein may include two different Fourier filter embodiments, one deviated and one non-deviated. The Fourier filters may then be moved into and out of the illumination and light collection paths of the inspection system depending on whether complete blocking of the diffracted light is desired or if some leakage of diffracted light is desired.

The embodiments of the Fourier filters described herein are advantageous in that the imaging aperture is configured such that it does not produce distortion in images of the wafer generated by the inspection system in which the Fourier filters are included. For example, the Fourier filter embodiments described herein will not produce distortion such as ringing at the image plane of the inspection system. In this manner, the Fourier filter embodiments described herein can be used to enhance defect detection on wafer patterns that are strongly directional such as line arrays without side-effects of conventional Fourier filters such as ringing.

Figure 11:
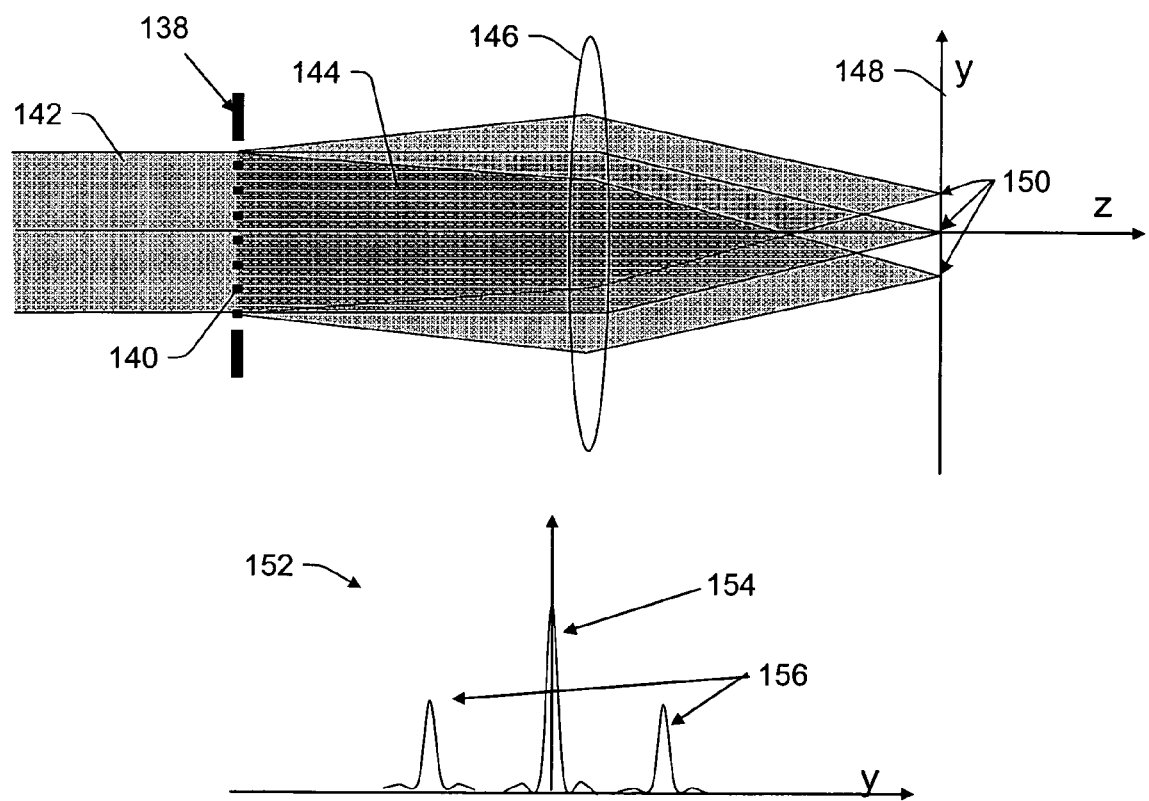
FIG. 11 is a schematic diagram illustrating a side view of a previously used Fourier filter and image artifacts caused by the Fourier filter.

In contrast, some laser-based dark field inspection tools are configured to image a patterned wafer using a Fourier filter that includes a number of substantially opaque elements that can be positioned to block light diffracted from structures on the patterned wafers. One example of such a Fourier filter is illustrated in FIG. 11. As shown in FIG. 11, Fourier filter 138 includes a number of substantially opaque elements 140 that are positioned in a path of light 142 from a wafer (not shown in FIG. 11). Substantially opaque elements 140 are positioned to block light diffracted from structures (not shown in FIG. 11) on a patterned wafer. Light 144 that passes through Fourier filter 138 is imaged by imaging lens 146 onto image plane 148.

If too many substantially opaque elements 140 are positioned in the imaging path of the inspection system, individual pixels on the wafer may be imaged at more than one pixel 150 on imaging plane 148 producing side-lobe like effects in the images of the wafer. Such distortion in the image is generally caused by diffraction of the light by the repetitive disruption of the opaque elements of the Fourier filter in a manner similar to light being diffracted by a grating.

Such distortion is illustrated in image intensity profile 152 shown in FIG. 11 that is produced at image plane 148 by Fourier filter 138 and imaging lens 146. As shown in image intensity profile 152, image 154 of a point from the wafer has the highest intensity in the image intensity profile. However, side lobes 156 (or ringing) caused by periodic Fourier filter 138 also appear in the image intensity profile. As described above, side lobes 156 are caused by diffraction of light by the periodic Fourier filter blockage. Side lobes 156 have a lower intensity than image 154. The intensity of side lobes 156, however, may be sufficient to cause distortion of image 154. In contrast to the Fourier filter shown in FIG. 11, the embodiments of the Fourier filters described herein have a continuous opening without any disruption in the imaging aperture. Therefore, the embodiments of the Fourier filters described herein will not cause distortion such as ringing at the image plane.

The Fourier filter embodiments described herein also have a number of additional advantages over conventional Fourier filters. For instance, as described above, the Fourier filter embodiments described herein can block 0th order light and all higher orders of diffraction by one-dimensional array patterns and some two-dimensional array patterns that have strong asymmetric cell structures. In this manner, the Fourier filter embodiments described herein provide substantially complete blockage of all diffraction orders from one-dimensional arrays of patterned structures and highly asymmetric two-dimensional arrays. In addition, the embodiments of the Fourier filter described herein are extremely simple to implement and are completely compatible with existing bright field wafer inspection systems. In this manner, the Fourier filters described herein are relatively low cost. Furthermore, the embodiments of the Fourier filters described herein have the same light efficiency as other conventional dark field apertures described herein.

Moreover, dark field imaging mode on current bright field tools consistently shows greater value than bright field imaging modes. A fundamental mechanism contributing to the higher value of the dark field imaging mode is the elimination of background noise from the output signals generated by the inspection system thereby producing higher defect detection sensitivity. As described above, conventional dark field mode may allow some of the diffraction orders to pass through the imaging aperture resulting in higher background and pattern noise in the detector images. However, the Fourier filter embodiments described herein substantially eliminate such background noise for one-dimensional arrays and some two-dimensional arrays that have a relatively large pitch in one direction by using substantially simple one-dimensional apertures. The implementation of such Fourier filters is relatively low cost and can be easily installed on all existing bright field wafer inspection systems. Therefore, a relatively large number of inspection layers can benefit from this technology. Consequently, the ratio of performance improvements to cost is substantially large.

Although Fourier filter embodiments are described herein as being configured to be included in imaging inspection systems, it is to be understood that the Fourier filter embodiments may be included in inspection systems having other types of architecture (i.e., non-area imaging systems). For example, the Fourier filter embodiments described herein may be included in a spot scanning type inspection system such as the systems illustrated in U.S. Pat. Nos. 6,809,808 to Feldman et al., 6,853,475 to Feldman et al., and 6,882,417 to Goldberg et al., and U.S. Patent Application Publication No. US 2004/0235208 to Reinhorn, which are incorporated by reference as if fully set forth herein.

The Fourier filter embodiments described herein are also configured such that performance of the Fourier filters is substantially independent of wavelength used for inspection. In particular, the Fourier filter embodiments described herein are configured to block diffraction orders independent of wavelength, which is critical for broadband imaging. Such blocking of diffraction orders in broadband imaging is much more difficult than in laser-based systems since broadband light sources are not point light sources, and therefore a well defined diffraction pattern at the back focal plane of the objective cannot be obtained with practically useful light efficiency. In addition, the diffraction orders for broadband illumination are wavelength dependent and may be relatively blurred and larger at the pupil plane than diffraction orders resulting from illumination by a point light source. In contrast, with laser-based dark field systems, at the pupil plane of the systems, the diffraction pattern has a relatively regular structure, which provides for relatively efficient filtering using conventional Fourier filters. As such, Fourier filters that are configured for use with lasers or other single point light sources are generally unsuitable for use in broadband imaging systems.

According to one embodiment, therefore, a Fourier filter configured to be included in a wafer inspection system includes an asymmetric illumination aperture that is configured to be positioned in an illumination path of the inspection system. The illumination aperture may be further configured as described herein. This embodiment of a Fourier filter also includes an asymmetric imaging aperture that is complementary to the illumination aperture. The imaging aperture is configured to be positioned in a light collection path of the inspection system such that the imaging aperture blocks light reflected and diffracted from structures on the wafer and allows light scattered from defects on the wafer to pass through the imaging aperture. The imaging aperture may be further configured as described herein. Performance of the Fourier filter is substantially independent of wavelength of the wafer inspection system. This embodiment of a Fourier filter may be further configured according to any other embodiment(s) described herein.

All of the Fourier filter embodiments described herein may be fabricated in any manner and using any materials known in the art. For example, the illumination and imaging apertures may be formed of metal or another suitably opaque material having openings formed therein. In another example, the illumination and imaging apertures may include metal or other suitably opaque structures formed on a substantially transparent substrate such as glass. Obviously, the materials of which the illumination and imaging apertures are formed may vary depending on the wavelengths of illumination used by the inspection system in which the apertures will be included. In addition, the dimensions of the apertures may vary depending on the configuration of the inspection system in which the apertures will be included. Each of the embodiments of the Fourier filters described above may be further configured according to any other embodiment(s) described herein.

Figure 12:
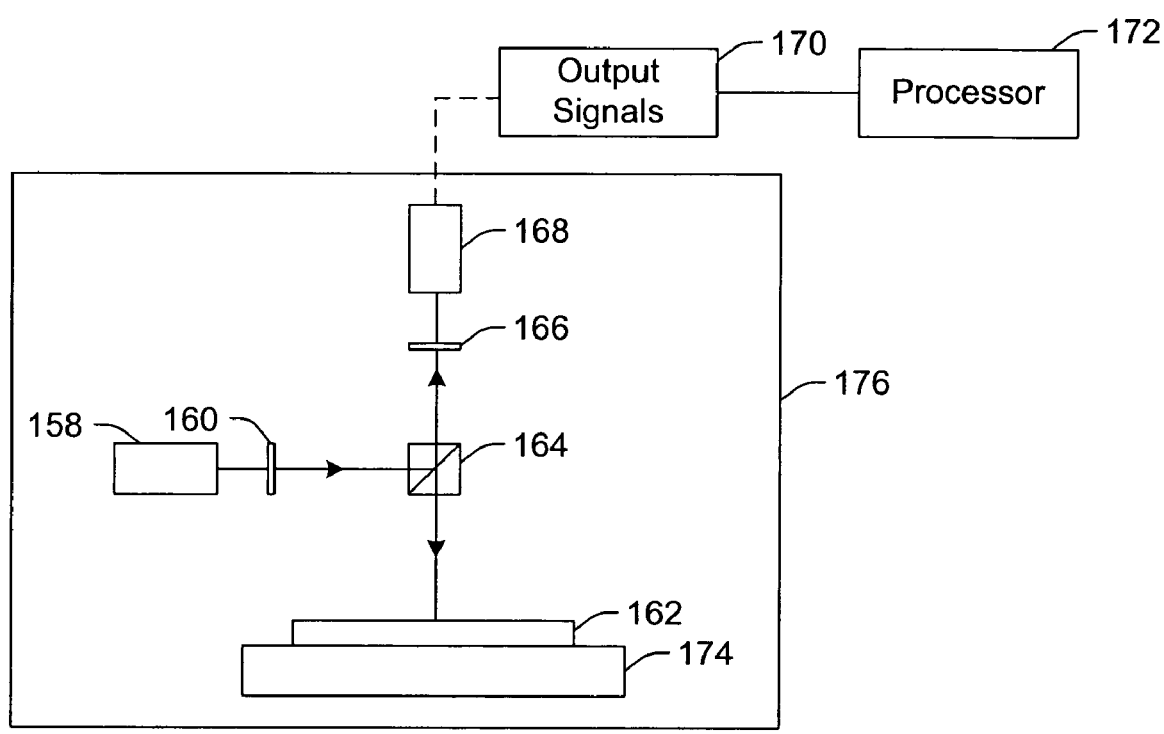
FIG. 12 is a schematic diagram illustrating a side view of one embodiment of a system configured to inspect a wafer.

Another embodiment relates to a system configured to inspect a wafer. One such embodiment of a system is illustrated in FIG. 12. As shown in FIG. 12, the system includes broadband light source 158 configured to generate incoherent light. Light source 158 may include any suitable broadband light source known in the art. For example, the light source may be a white light source. In addition, the light source may be an arc lamp or a mercury-xenon (HgXe) arc lamp. Furthermore, the light source may be configured to emit light having a broadband wavelength range from the deep ultraviolet (DUV) wavelength regime to the infrared (IR) wavelength regime. In one particular example, the light source may be configured to emit light having wavelengths from about 250 nm to about 500 nm.

The system shown in FIG. 12 also includes asymmetric illumination aperture 160 arranged in a path of the light generated by broadband light source 158 such that light that passes through the illumination aperture illuminates wafer 162. In particular, light that passes through illumination aperture 160 may be directed to wafer 162 by beam splitter 164. Beam splitter 164 may include any suitable optical component known in the art. In addition, or alternatively, light that passes through illumination aperture 160 may be directed to wafer 162 by one or more other optical components (not shown) such as an objective lens. Illumination aperture 160 may be further configured as described herein.

Light reflected, diffracted, and scattered from wafer 162 passes through beam splitter 164. In addition, the inspection system may include one or more additional components (not shown) such as a pupil relay lens that images the back focal plane of the objective to an accessible plane. The system also includes asymmetric imaging aperture 166 that is complementary to illumination aperture 160 and located at the conjugate image plane of illumination aperture 160. Light that passes through beam splitter 164 is directed to imaging aperture 166. Imaging aperture 166 is configured to block light reflected and diffracted from structures (not shown in FIG. 12) on the wafer and to allow light scattered from defects (not shown in FIG. 12) on the wafer to pass through the imaging aperture. Imaging aperture 166 may be arranged at a Fourier plane (not shown) of the system.

When the illumination and imaging apertures are positioned in the illumination and collection paths as shown in FIG. 12, the inspection system can be used for broadband dark field inspection of wafer 162. However, the illumination and imaging apertures may be moved out of the illumination and collection paths, respectively, such that the inspection system can be used for bright field inspection of wafer 162. The apertures may be moved into and out of the illumination and light collection paths using any method and/or device known in the art.

Imaging aperture 166 may be further configured as described herein. For example, in one embodiment, a length of the imaging aperture is substantially perpendicular to a length of the structures formed on the wafer. In another embodiment, the light that is blocked by the imaging aperture includes light reflected and diffracted from structures on the wafer that extend lengthwise along a direction that is substantially perpendicular to a length of the imaging aperture. In an additional embodiment, the light that is blocked by the imaging aperture includes light reflected and diffracted from one-dimensional array patterns on the wafer. In some embodiments, the light that is blocked by the imaging aperture includes all orders of light diffracted from structures on the wafer.

In other embodiments, the light blocked by the imaging aperture does not include light reflected and diffracted from structures on the wafer that extend lengthwise along a direction that is not perpendicular to a length of the imaging aperture. In a further embodiment, a total open area of the illumination aperture is substantially equal to a total open area of the imaging aperture.

The system also includes detector 168 that is configured to generate output signals 170 responsive to light that passes through imaging aperture 166. In one embodiment, the imaging aperture is configured such that the imaging aperture does not produce distortion in the output signals generated by the detector. The detector may include a detector configured to form an image of the wafer. For example, the detector may be a charge-coupled device (CCD) or time delay integration (TDI) camera. As such, the inspection system shown in FIG. 12 may be configured as an imaging system. In this manner, the inspection system may be configured as a microscope type system.

Output signals 170 generated by detector 168 can be used to detect the defects on wafer 162. For example, the system may include processor 172. Processor 172 may be coupled to detector 168 by a transmission medium (not shown). The transmission medium may include any suitable transmission medium known in the art. In addition, the processor may be coupled to the detector by one or more electronic components (not shown) such as an analog-to-digital converter. In this manner, processor 172 is configured to receive output signals 170 from detector 168.

Processor 172 may be configured to use the output signals to detect defects on the wafer. In addition, the processor may be configured to use the output signals and any method and/or algorithm known in the art to detect the defects on the wafer. Furthermore, processor 172 may be configured to perform any other inspection-related functions known in the art (e.g., defect location determination, defect classification, defect mapping, etc.).

Processor 172 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

In some embodiments, the system shown in FIG. 12 is configured to alter one or more parameters of the illumination and imaging apertures based on characteristics of structures on the wafer. For instance, the system may include any suitable mechanical or other assembly (not shown) coupled to substantially opaque bars of the illumination and imaging apertures (such as those shown in FIG. 6). The mechanical or other assembly may be configured to effectuate movement of the substantially opaque bars of the apertures. In addition, the system may include two such assemblies, each of which is coupled to the opaque bars of the illumination or imaging aperture.

The assembly or assemblies may be coupled to a processor of the system (e.g., processor 172 or another processor of the system (not shown)) such that the assemblies may be controlled by the processor of the system. For example, processor 172 may be configured to receive or determine information about characteristics of wafer 162 to be inspected by the system shown in FIG. 12. The processor may then determine appropriate parameters of the illumination and imaging apertures for the characteristics of structures on the wafer and cause the assembly or assemblies to alter the parameters of the illumination and imaging apertures accordingly.

In a similar manner, in some embodiments, the system is configured to alter an angle of rotation of the illumination and imaging apertures based on characteristics of structures on the wafer. In additional embodiments, the system is configured to alter one or more parameters of the illumination and imaging apertures such that a portion of light diffracted from structures on the wafer passes through the imaging aperture.

The system shown in FIG. 12 may include any other suitable components known in the art. For instance, the system may include stage 174, which is configured to support wafer 162 during inspection. In addition, the stage may be configured to move the wafer during inspection such that the light can scan across the wafer. In some instances, the stage may be configured to move the wafer such that the light from beam splitter 164 moves over the wafer in an x y scan of the wafer. The stage may include any suitable mechanical or robotic assembly known in the art.

The system shown in FIG. 12 may also include housing 176, in which optical components of the system, the wafer, and the stage are disposed during inspection. The housing may serve a variety of functions such as reducing stray light incident on the wafer during inspection, providing a space in which environmental conditions can be controlled, etc. The housing may have any suitable configuration known in the art.

In some embodiments, the inspection systems described herein may be configured as "stand alone tools" or tools that are not physically coupled to a process tool. However, such a system may be coupled to a process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler. Alternatively, the inspection systems described herein may be integrated into a process tool such as those described above.

The results of inspection performed by the systems described herein may be used to alter a parameter of a process or a process tool using a feedback control technique, a feedforward control technique, and/or an in situ control technique. The parameter of the process or the process tool may be altered manually or automatically.

Further modifications and alternative embodiments of various aspects of the invention may be apparent to those skilled in the art in view of this description. For example, Fourier filters and wafer inspection systems are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A one-dimensional Fourier filter configured to be included in a bright field inspection system such that the bright field inspection system can be used for broadband dark field inspection of a wafer, the Fourier filter comprising:

an asymmetric illumination aperture configured to be positioned in an illumination path of the inspection system; and an asymmetric imaging aperture complementary to the illumination aperture, wherein the imaging aperture is configured to be positioned in a light collection path of the inspection system such that the imaging aperture blocks light reflected and diffracted from structures on the wafer and allows light scattered from defects on the wafer to pass through the imaging aperture.

2. The Fourier filter of claim 1, wherein the imaging aperture is further configured to be positioned in the light collection path such that a length of the imaging aperture is substantially perpendicular to a length of the structures.

3. The Fourier filter of claim 1, wherein the light blocked by the imaging aperture comprises light reflected and diffracted from the structures that extend lengthwise along a direction substantially perpendicular to a length of the imaging aperture.

4. The Fourier filter of claim 1, wherein the structures comprise one-dimensional array patterns.

5. The Fourier filter of claim 1, wherein the light blocked by the imaging aperture comprises all orders of light diffracted from the structures.

6. The Fourier filter of claim 1, wherein the light blocked by the imaging aperture does not comprise light reflected and diffracted from the structures that extend lengthwise along a direction that is not perpendicular to a length of the imaging aperture.

7. The Fourier filter of claim 1, wherein the imaging aperture is further configured such that a portion of light diffracted from the structures passes through the imaging aperture.

8. The Fourier filter of claim 1, wherein the illumination and imaging apertures are further configured such that one or more parameters of the illumination and imaging apertures can be altered based on characteristics of the structures.

9. The Fourier filter of claim 1, wherein the illumination and imaging apertures are further configured such that an angle of rotation of the illumination and imaging apertures can be altered based on characteristics of the structures.

10. The Fourier filter of claim 1, wherein a total open area of the illumination aperture is substantially equal to a total open area of the imaging aperture.

11. The Fourier filter of claim 1, wherein the imaging aperture is further configured such that the imaging aperture does not produce distortion in images of the wafer generated by the inspection system.

12. A Fourier filter configured to be included in a wafer inspection system, comprising:

an asymmetric illumination aperture configured to be positioned in an illumination path of the inspection system; and an asymmetric imaging aperture complementary to the illumination aperture, wherein the imaging aperture is configured to be positioned in a light collection path of the inspection system such that the imaging aperture blocks light reflected and diffracted from structures on the wafer and allows light scattered from defects on the wafer to pass through the imaging aperture, and wherein performance of the Fourier filter is substantially independent of wavelength of the wafer inspection system.

13. A system configured to inspect a wafer, comprising:
a broadband light source configured to generate incoherent light;

an asymmetric illumination aperture arranged in a path of the light such that light that passes through the illumination aperture illuminates the wafer;

an asymmetric imaging aperture complementary to the illumination aperture, wherein the imaging aperture is configured to block light reflected and diffracted from structures on the wafer and to allow light scattered from defects on the wafer to pass through the imaging aperture; and a detector configured to generate output signals responsive to the light that passes through the imaging aperture, wherein the output signals can be used to detect the defects on the wafer.

14. The system of claim 13, wherein the imaging aperture is arranged at a Fourier plane of the system.

15. The system of claim 13, wherein a length of the imaging aperture is substantially perpendicular to a length of the structures.

16. The system of claim 13, wherein the light blocked by the imaging aperture comprises light reflected and diffracted from the structures that extend lengthwise along a direction substantially perpendicular to a length of the imaging aperture.

17. The system of claim 13, wherein the structures comprise one-dimensional array patterns.

18. The system of claim 13, wherein the light blocked by the imaging aperture comprises all orders of light diffracted from the structures.

19. The system of claim 13, wherein the light blocked by the imaging aperture does not comprise light reflected and diffracted from the structures that extend lengthwise along a direction that is not perpendicular to a length of the imaging aperture.

20. The system of claim 13, wherein the system is further configured to alter one or more parameters of the illumination and imaging apertures based on characteristics of the structures.

21. The system of claim 13, wherein the system is further configured to alter an angle of rotation of the illumination and imaging apertures based on characteristics of the structures.

22. The system of claim 13, wherein the system is further configured to alter one or more parameters of the illumination and imaging apertures such that a portion of light diffracted from the structures passes through the imaging aperture.

23. The system of claim 13, wherein a total open area of the illumination aperture is substantially equal to a total open area of the imaging aperture.

24. The system of claim 13, wherein the imaging aperture is further configured such that the imaging aperture does not produce distortion in the output signals generated by the detector.

* * * * *